(12) United States Patent
Fierens et al.

(10) Patent No.: US 8,652,099 B2
(45) Date of Patent: Feb. 18, 2014

(54) DEVICE FOR DELIVERING MEDICAL TREATMENT

(75) Inventors: Joost J. Fierens, Dworp (BE); Eric Marcoux, Ecaussinnes (BE); Malika Omari, Schaerbeek (BE)

(73) Assignee: Medical Device Works NV SA, Brussels (BE)

(*) Notice: Subject to any disclaimer, the term of this patent is extended or adjusted under 35 U.S.C. 154(b) by 450 days.

(21) Appl. No.: 12/293,354

(22) PCT Filed: Mar. 20, 2007

(86) PCT No.: PCT/EP2007/002445
§ 371 (c)(1),
(2), (4) Date: Sep. 17, 2008

(87) PCT Pub. No.: WO2007/107327
PCT Pub. Date: Sep. 27, 2007

(65) Prior Publication Data
US 2009/0112184 A1    Apr. 30, 2009

(30) Foreign Application Priority Data
Mar. 20, 2006 (EP) .................................. 06447039

(51) Int. Cl.
*A61M 37/00* (2006.01)
(52) U.S. Cl.
USPC ................. 604/104; 604/101.01; 604/101.03; 604/101.04; 604/101.05; 604/103.01
(58) Field of Classification Search
USPC ............... 604/95.05, 101.01, 101.03–101.05, 604/103.01, 104; 606/192–194, 200
See application file for complete search history.

(56) References Cited

U.S. PATENT DOCUMENTS

| 4,795,427 | A | * | 1/1989 | Helzel ............................... 604/9 |
| 4,883,459 | A |   | 11/1989 | Calderon |
| 5,366,504 | A | * | 11/1994 | Andersen et al. .............. 623/1.5 |

(Continued)

FOREIGN PATENT DOCUMENTS

| WO | WO 99/30765 | 6/1999 |
| WO | WO 00/76390 | 12/2000 |
| WO | WO 2005/014100 | 2/2005 |

OTHER PUBLICATIONS

Savier, et al. "Percutaneous Isolated Hepatic Perfusion for Chemotherapy, A Phase I Study," *Arch Surg*, vol. 138, pp. 325-332, Mar. 2003.

(Continued)

*Primary Examiner* — Kami A Bosworth
*Assistant Examiner* — Larry R Wilson
(74) *Attorney, Agent, or Firm* — Knobbe Martens Olson & Bear LLP

(57) ABSTRACT

A medical device for the delivery of treatment fluid to body vessels is described. The device has a distal (21) and a proximal (20) end with a self-expanding, hollow tubular member (9) and a delivery catheter (10) suitable for deploying a self-expanding, tubular member (9). The tubular member (9) is configured to expand radially to form a central part (11) flanked by two annular ridges, which creates, in situ, an annular lumen that can apply treatment fluid locally to a vessel and a passageway that can maintain the flow of blood through the vessel. The device is particularly suited for minimally invasive and repeatable organ perfusion. A method for organ perfusion is also disclosed.

14 Claims, 6 Drawing Sheets

(56) References Cited

U.S. PATENT DOCUMENTS

| | | | |
|---|---|---|---|
| 5,817,046 A | 10/1998 | Glickman | |
| 5,868,708 A | 2/1999 | Hart et al. | |
| 5,919,224 A * | 7/1999 | Thompson et al. | 606/200 |
| 6,139,517 A * | 10/2000 | Macoviak et al. | 604/8 |
| 6,162,237 A * | 12/2000 | Chan | 606/198 |
| 2003/0028211 A1 | 2/2003 | Crocker et al. | |
| 2005/0124849 A1 | 6/2005 | Barbut et al. | |

OTHER PUBLICATIONS van Etten, et al. "Isolated Hypoxic Hepatic Perfusion with Orthograde or Retrograde Flow in Patients with Irresectable Liver Metastases Using Percutaneous Balloon Catheter Techniques: A Phase I and II Study," *Annals of Surgical Oncology*, vol. 11, No. 6, pp. 598-605, 2004.

International Search Report dated Jul. 13, 2007.

* cited by examiner

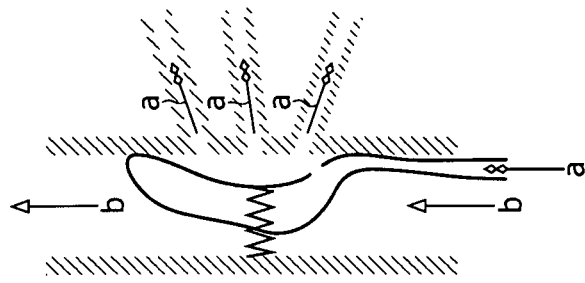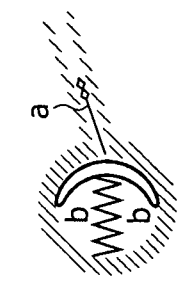
FIG. 4E
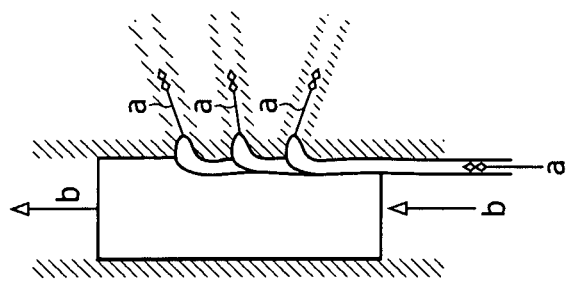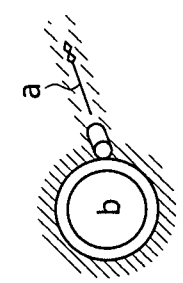
FIG. 4D
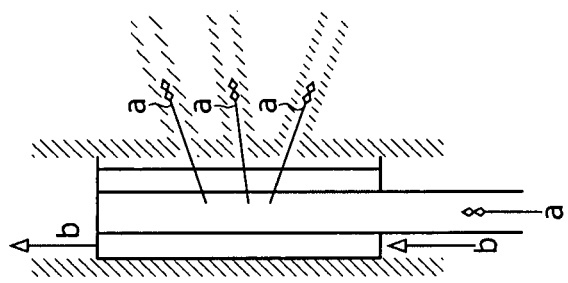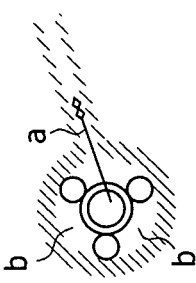
FIG. 4C
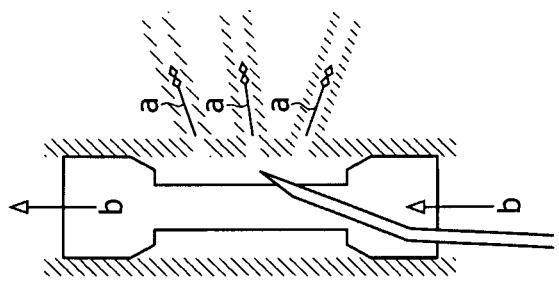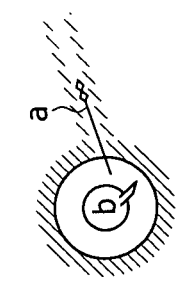
FIG. 4B
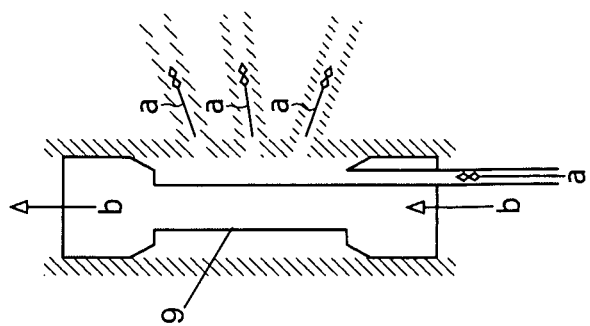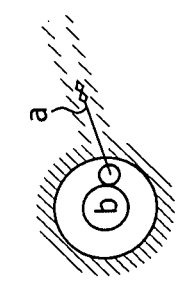
FIG. 4A

DEVICE FOR DELIVERING MEDICAL TREATMENT

CROSS-REFERENCE TO RELATED APPLICATIONS

This application is the U.S. National Phase under 35 U.S.C. §371 of International Application PCT/EP2007/002445, filed Mar. 20, 2007, which claims priority to EP 06447039.6, filed Mar. 20, 2006.

FIELD OF THE INVENTION

The present invention relates to a device for delivering medical treatment, preferably a treatment fluid to a localised region of a vessel. The invention may be used to provide a minimally invasive isolation and perfusion of an organ with a perfusion fluid, thereby enhancing the effectiveness of the treatment and improving the quality of the patient's life during and after treatment. More specific, the invention provides a device, formed such that, when positioned in a blood vessel, the device defines a flow path for the systemic blood, isolated from the cavity created for the treatment fluid. The invention also describes a system and its use, wherein said device is combined with a delivery catheter, delivering the treatment fluid to said cavity. Furthermore, the invention also provides four other systems suitable for minimally invasive isolation and perfusion of an organ.

BACKGROUND OF THE INVENTION

Treatment with systemic chemotherapy is one of the presently used possibilities for cancer treatment. However, substances that are effective in this kind of treatment are often harmful to the system of the body as a whole. Particularly, the treatment of cancer of the liver presents a serious clinical problem, and the success rate when treating liver cancer is today very low.

Although primary liver cancer (hepatoma) is rather uncommon in northern Europe and United States, hepatoma is prevalent in other parts of the world, e.g. in Southeast Asia, Japan, the Pacific Islands, Greece, Italy and parts of Africa. Also, many patients with cancer in the gastrointestinal tract develop isolated hepatic metastases, since the liver is the primary target for dissemination. Due to the distribution of the metastases within the liver, only few patients with liver cancer can be cured by resection.

Liver cancer is today mainly treated with systemic chemotherapy. However, no substantial increase in the time of survival of the patients is following this treatment (L. M. De Brauw "*Isolated liver perfusion. An experimental modality in the treatment of hepatic metastases.*" Thesis, University of Leiden, Leiden, The Netherlands). A reason for these discouraging results seems to be the fact that the toxicity of the chemodrugs limits the possible dosage due to the systemic effects. Local administration by infusion in the hepatic artery does not solve this problem, since the chemodrugs are distributed in the system also during this procedure.

Therefore, it has been suggested that therapeutic drugs should be administered locally by isolation of a vessel wall, by performing perfusion of the liver or other selected isolated organs.

To be therapeutically successful, a treatment session must be applicable one or several times in a treatment cycle (1 to 6 times or more) during a predetermined time interval. Individual treatment sessions can have durations of several minutes to hours, and can have intervals of several days or weeks. The technique must, therefore, be repeatable and the devices used for each individual treatment should be retrievable to reestablish the pre-interventional situation after each treatment session. To realize repeatability, the technique has to be least traumatic which requires minimally invasive i.e. percutaneous techniques.

Examples of techniques for isolating and perfusing organs are found for example in the following prior art documents.

In EP-0 364 799 to BGH Medical Products, a process of perfusing a high concentration of an agent through an organ is described. The agent is infused arterially in the organ and on the venous side of the organ the blood is removed from the body using a specially designed double balloon catheter. In this process there is a leakage to the systemic blood flow, since there are numerous blood communicating vessels besides the main artery and the main vein.

A similar catheter is used in the U.S. Pat. No. 5,817,046 to Glickman et al., showing a system for perfusion of the pelvic cavity. The pelvic cavity is isolated between a double catheter, placed in the iliac vein, and bilateral thigh tourniquets. The thigh tourniquets, which are used to restrict the flow of blood between the legs and the pelvic cavity of the patient, limit the time during which perfusion can be performed.

In U.S. Pat. No. 4,714,460 to Calderon, feedback methods and systems for retrograde perfusion in the body are described. A double balloon concentric catheter, with an inner infusion lumen and an outer suction lumen, is used for perfusion of the venous side of the vascular network. The therapeutic agent for treatment is infused inside the vein in the opposite direction with respect to the ordinary blood flow, also called retrograde infusion. The described method is, thus, designed to operate in back pressure and the perfusion fluid is continuously diluted by arterial blood.

U.S. Pat. No. 4,883,459 to Calderon describes a method for perfusion where a carrier medium dye is injected into the tumor. The flow of the dye is monitored to determine an optimal retrograde perfusion path through the tumor.

A balloon catheter with closed tip and device for perfusion with such catheters, are described in U.S. Pat. No. 5,746,717 to Aigner. The catheter has at least one contrast marking which enables the position of the catheter inside the body to be determined.

The perfusion processes and apparatuses described above all include the return of the blood, which has been contaminated with drugs, to the systemic circulation. This requires treatment to remove the contaminants before this blood can be returned to the body. Also, by not isolating the organ in a perfusion circuit, as is the case in some of the above mentioned procedures, perfusion fluid may easily leak into the systemic circulation. Furthermore, most catheters explained above have the disadvantage that they remain in the body of the living being after termination of the perfusion process.

WO 83/03535 to Cromie describes a liver perfusion bypass member defining three flow conduits. The first conduit, formed by one or more lumens extending along the entire length of the member, provides a flow path for the systemic blood. The second flow conduit, formed by a sealed longitudinal lumen, receives the blood of the liver which is recycled back to the liver by the third conduit, connected to the second one. In this third conduit a system is provided for delivering the therapeutic agent. After treatment the blood in the second and third conduit is removed and would not be returned to the patient.

A similar double perfusion catheter is provided by U.S. Pat. No. 4,540,402 to Aigner. This catheter also defines two blood flows. The first one is the systemic blood flow which is guided through a first catheter tube. The second flow, the perfusion flow, is conducted to a heart-lung machine by a second catheter tube, mounted on the first tube, and this flow is recycled through the liver.

Both devices described above provide continuation of the systemic blood flow during isolation and perfusion of the liver so perfusion can be performed with higher concentrations of therapeutic agent and during a longer period of time. A major disadvantage however is that said devices have to be inserted and removed by open surgery, only permitting perfusion once due to scars in the tissues and the severe stress on the body of the patient.

U.S. Pat. No. 6,287,273 to Allers et al. describes a system for isolated perfusion without the need for surgery, consisting of a catheter set, a pump apparatus and perfusion control apparatus. The method comprises isolating an organ by placing occlusive seals in the most important blood vessels of the organ and establishing a bypass circuit for the systemic blood and a perfusion circuit connected to the organ. Both circuits are partially extracorporeal, whereby the therapeutic agent is administered to the perfusion circuit outside the body.

WO 03/006096 to Allers et al. provides a catheter, delivered endoluminally, which can replace the occlusive seals used in the method described in U.S. Pat. No. 6,287,273. In one embodiment the catheter stem is fluid permeable while the structure at the end of the catheter is fluid impermeable, thereby restricting venous blood entering the vena cava and allowing the systemic blood to flow through the catheter. Another embodiment describes a fluid impermeable stem and a fluid permeable end structure, thereby allowing delivery of therapeutic agents to the hepatic veins while blocking the systemic blood flow through the vena cava.

A disadvantage of the invention in these documents is the complexity of the method. For example, perfusion of the liver demands positioning of at least four to five catheters. One or two catheters are placed into the inferior vena cava for isolating systemic from liver blood flow, another catheter is placed in the vena porta and guides the systemic blood to the catheter placed in the superior vena cava while conducting the perfusion flow to the catheter positioned in the hepatic artery. Furthermore, the fluid is circulated in the extracorporeal circuits by pumping and has to be monitored carefully by control devices to ensure, for example, blood pressure and temperature. Furthermore, many rely on occlusion using an inflatable balloon, which are prone to leakage.

As can be noticed by the amount of prior art documents mentioned above, much effort has already been made for providing methods, devices and systems for isolating and perfusing an organ affected with cancer with therapeutic drugs. However, all these methods, devices and systems have their limitations and drawbacks, so there is a persistent need for improvement to and/or simplification of the prior art. Especially for treatment of liver cancer strong progress is demanded.

OBJECT OF THE INVENTION

The object of the present invention is to provide a device and system for delivering a medical treatment to a localised region of a vessel. The invention may be used to provide a minimally invasive isolation and perfusion of an organ with a therapeutic agent, thereby enhancing the effectiveness of the treatment and improving the quality of the patient's life during and after treatment. More specifically, the invention aims to deliver a device, formed such that, when positioned in a blood vessel, the device provides a flow path for the systemic blood, isolated from a cavity created for the perfusion fluid or other medical treatment fluid. Another object of the invention is to provide a device and its use, wherein said device is combined with a delivery catheter, delivering the treatment fluid to said cavity. Furthermore, the invention also aims to provide four other systems suitable for minimally invasive isolation and perfusion of an organ.

SUMMARY OF THE INVENTION

The present invention provides an expandable medical device suitable for delivering a medical treatment to a localised region of a vessel. The device comprises a self-expanding tubular member that is radially expandable and wherein the central part of the member is configured to expand to a lesser degree compared to the ends of the tubular member. In the non-expanded state the device can be more easily maneuvered inside a blood vessel and become expanded when at the desired position. The central part is configured to expand cylindrically while the ends are configured to expand conically. This way the tubular member creates a cavity between the device and the inner wall of the vessel. The end parts of the device are configured to provide a liquid tight seal in the vessel, thereby isolating said cavity from the systemic blood flow.

The device according to the present invention is formed by at least a carrier and a liquid impermeable liner. The carrier renders the device its expandability by self-expansion and is preferentially made of a self-expandable braided wire mesh. In an embodiment, the carrier is made from a surgical wire preferably of an alloy comprising Cobalt, Chromium, Nickel, Molybdenum and Iron, and more preferably a surgical wire in accordance to ASTM F 1058. Other carriers are within the scope of the invention made of, for example, shape memory alloy or synthetic material are applicable. They may be woven from wire or laser cut. The liner renders the device its liquid impermeability and is made from a biocompatible material, by preference a medical grade polycarbonate polyurethane formulation.

The device of the invention further comprises a passageway that extends through the entire length of the tubular member and is bordered by the liner. This lumen is configured to guide the systemic blood past the liquid tight seal and isolated cavity by providing a flow path through the device.

The present invention further comprises a delivery catheter, which is responsible for delivering a medical treatment fluid to the isolated cavity formed between the device and the inner wall of the blood vessel. In one embodiment said delivery catheter is configured to be connected to a flush opening in the liner in contact with said isolated cavity. In another embodiment the delivery catheter is configured to pierce through the liner without interfering with the liners liquid impermeability.

The present invention also describes a use of said device for minimally invasive isolating and perfusing the liver of a living being. Hereby said device is positioned into the inferior vena cava. The device blocks the flow path of blood in the inferior vena cava by providing a liquid tight seal in the blood vessel, while a lumen through the device forms a flow path and guides the systemic blood through the device. The device further creates a cavity between itself and the inner wall of the vena cava, whereby the cavity is isolated from the systemic blood and is in contact with the liver by the hepatic veins arriving in the vena cava. Finally, the delivery catheter of said device guides the perfusion fluid into said cavity from where perfusion of the liver can be started.

The present invention further provides a system comprising a liquid impermeable tube and three or more expandable balloons or cylinders. The tube, having a flush opening and being closed at its distal end, is configured to deliver the perfusion fluid. The balloons or cylinders, placed longitudinally relative to the tube, at different sites and at or near its distal end, are connected to the outside of the tube. The balloons or cylinders around the flush opening are also connected at their extremities. After positioning, the balloons or cylinders become expanded, thereby creating a drug chamber around the hepatic veins and assuring that the system remains closed and in position.

Another system, described by the present invention, comprises one or more tubes and a liquid impermeable stent. The tube or tubes are configured to deliver a perfusion fluid to an organ and are placed in a vessel with their ends in one or more adjacent input and/or output vessels of said organ. Subsequently the stent is placed in said vessel in such that it pushes the tube or tubes into the wall of the vessel, thereby providing a flow path for the systemic blood, isolated from the flow with perfusion fluid.

The present invention also provides a system comprising a liquid impermeable tube and a fixation means. This tube has a distal closed end formed as a cup or spoon, which, after positioning, creates a cavity in a blood vessel, isolated from the systemic blood. The tube also comprises a lumen, extending through it and ending in a flush opening in the concave wall of the cup or spoon form, guiding the perfusion fluid into said cavity.

One embodiment of the invention is a retrievable medical device for the delivery of medical treatment fluid to body vessels, having a distal (21) and a proximal (20) end, comprising a self-expanding, hollow tubular member (9) and a delivery catheter (10) suitable for deploying a self-expanding tubular member (9), wherein:
   the tubular member (9) is configured to expand radially to form a central part (11) flanked by two annular ridges—a distal annular ridge (12) and a proximal annular ridge (13),
   the tubular member (9) comprises a liquid-impermeable area, defined at least by the region flanked by the annular ridges (12, 13),
   the tubular member (9) comprises two liquid-permeable regions, one distal to the distal annular ridge (12) and one proximal to the proximal annular ridge (13), so forming a passageway (14) between the distal end (21) and the proximal end (20) of the tubular member (9) for the flow of fluid,
   the proximal end (20) of the tubular member (9) is attached to the distal end (21) of the delivery catheter (10),
   the liquid-impermeable area is disposed with one or more fluid ports (15) for the passage of treatment fluid.

Another embodiment of the invention is a device as described above, wherein the tubular member comprises:
   a liquid-permeable carrier (2) configured to adopt an essentially cylindrical state when compressed, and to self-expand radially to form a central part (11) flanked by two annular ridges (12, 13),
   a liner attached to the wall of the tubular member, which provides the liquid impermeable area.

Another embodiment of the invention is a device as described above, wherein carrier (2) is made of a braided wire mesh.

Another embodiment of the invention is a device as described above, wherein carrier (2) is made from a surgical wire that is:
an alloy comprising Cobalt, Chromium, Nickel, Molybdenum and Iron, or nitinol, or
a surgical wire in accordance to the standard ASTM F 1058.

Another embodiment of the invention is a device as described above, wherein carrier (2) is laser cut.

Another embodiment of the invention is a device as described above, wherein carrier (2) is made from any of polycarbonate polyurethane formulation, polytetrafluoroethylene, polyurethane, silicone or polyethylene terephthalate polymer.

Another embodiment of the invention is a device as described above, wherein the catheter (10) comprises:
(a) an inner tube (5);
(b) an outer tube (3), and
(c) a pusher means (23) for deployment of the tubular member (9),
   the outer tube (3) surrounding at least a portion of the length of the inner tube (6),
   the pusher means (23) being:
      a pusher rod (4) disposed between the inner tube (5) and the outer tube (3), or
      formed from the wall of the inner tube (5),
   the pusher means (23) being adapted for axial movement relative to the outer tube (3),
   the proximal end of the tubular member (9) being attached to the distal end of the pusher means (23), and disposed within the outer tube (3) in the compressed state.

Another embodiment of the invention is a device as described above, wherein the inner tube (5) is configured for the passage of treatment fluid.

Another embodiment of the invention is a device as described above, wherein the inner tube (5) is further configured to receive a guidewire.

Another embodiment of the invention is a device as described above, wherein the inner tube (5) of the catheter (10) is in fluid connection with the one or more ports (15).

Another embodiment of the invention is a device as described above, wherein the inner tube (5) of the catheter (10) is in fluid connection with the one or more ports (15), using a bridging tubing (19).

Another embodiment of the invention is a device as described above, wherein the tubular member (9) is configured to create a fluid impermeable annular cavity (18) between said device and the inner wall of the vessel.

Another embodiment of the invention is a device as described above, wherein the proximal end (20) of the tubular member (9) is non-releasably attached to the distal end (21) of the delivery catheter (10), Another embodiment of the invention is a kit comprising:
   a device as defined above, and one of more of the following:
   an occlusion device for the hepatic artery, optionally with perfusion capacity,
   an occlusion device, with options for perfusion and shunting,
   one or more perfusion lines,
   one or more perfusion lines in fluid connection with a means for drawing medicament or perfusion fluid into a perfusion circuit, and
   one or more perfusion lines perfusion lines in fluid connection with at least one connector for drawing medicament or perfusion fluid into a perfusion circuit, said connector being specific to a particular medicine container.

Another embodiment of the invention is a use of a device as described above, for minimal invasive and repeatable organ perfusion of a living being by positioning the device into the inferior vena cava, thereby:
   a. blocking the flow path of blood in the inferior vena cava;
   b. providing a flow path for the blood through the passageway (14) of the device;

c. creating an isolated cavity (18) between the medical device and the wall of the vena cava, which is in contact with the liver by the hepatic veins; and d. delivering the perfusion fluid to or from this cavity by means of the delivery catheter.

Another embodiment of the invention is a use as described above, further comprising the step of withdrawing the device after perfusion.

BRIEF DESCRIPTION OF THE FIGURES

FIG. 1A shows a transverse cross-section across the catheter where the pusher means is a pusher rod. FIG. 1B shows a transverse cross-section across the catheter where the pusher means is formed from the wall of the inner tube.

FIG. 3 illustrates the device of the present invention have been placed in situ, wherein:

A illustrates a liner on the exterior of the carrier, and

B illustrates a liner on the interior of the carrier.

FIG. 4 shows a schematic sectional top and front view of five different systems of the present invention positioned in a blood vessel, whereby:

A illustrates a device comprising a dumb-bell shaped device and part of the delivery catheter connected to each other, B illustrates a system comprising a dumb-bell shaped device and a delivery catheter formed as a needle, C illustrates a system comprising a tube surrounded by three balloons or cylinders, D illustrates a system comprising three tubes pressed into the wall by a stent, and E illustrates a system comprising a fixation means and a tube with a cup or spoon shaped end.

Figure 5:
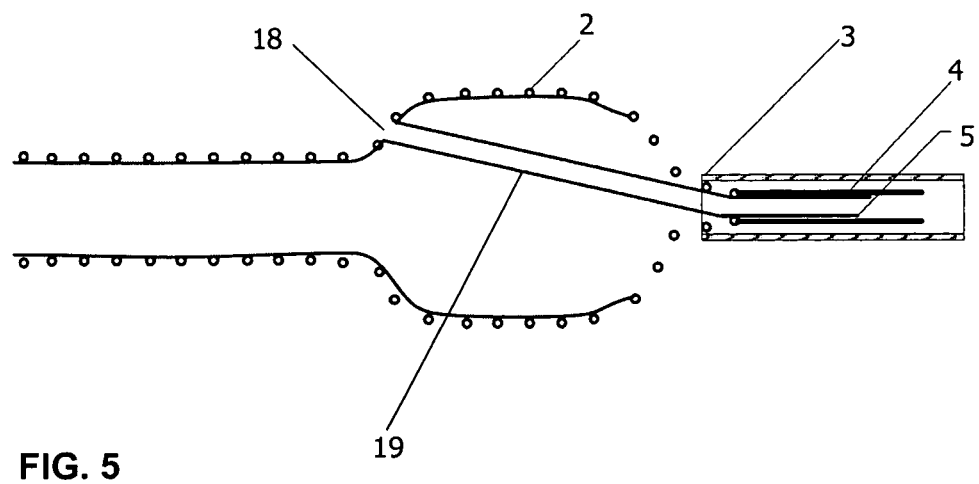
Figure 6:
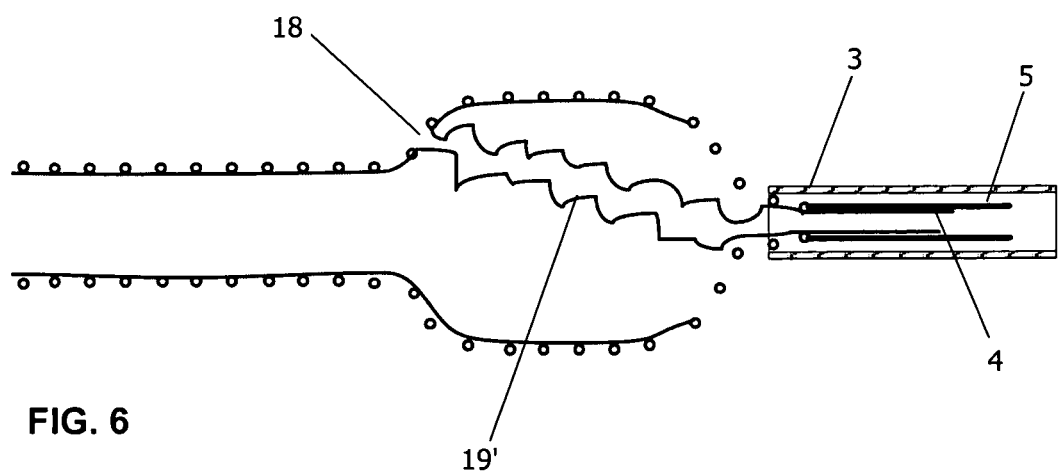

FIGS. 5 and 6 illustrates a device of the present invention, whereby a bridging tube is used to connect the inner tube to the port that accesses the annular lumen.

DETAILED DESCRIPTION OF THE INVENTION

Unless defined otherwise, all technical and scientific terms used herein have the same meaning as is commonly understood by one of skill in the art. All publications referenced herein are incorporated by reference thereto. All United States patents and patent applications referenced herein are incorporated by reference herein in their entirety including the drawings.

The articles "a" and "an" are used herein to refer to one or to more than one, i.e. to at least one of the grammatical object of the article. By way of example, "a port" means one port or more than one port.

Throughout this application, the term "about" is used to indicate that a value includes the standard deviation of error for the device or method being employed to determine the value.

The recitation of numerical ranges by endpoints includes all integer numbers and, where appropriate, fractions subsumed within that range (e.g. 1 to 5 can include 1, 2, 3, 4 when referring to, for example, a number of ports, and can also include 1.5, 2, 2.75 and 3.80, when referring to, for example, distances). The recitation of end points also includes the end point values themselves (e.g. from 1.0 to 5.0 includes both 1.0 and 5.0)

The present invention relates to a medical delivery device for providing local treatment to vessel walls or for the isolation and treatment of branched vessels. The device is particularly suited for the repeatable minimally invasive isolation and perfusion of an organ in a living being. The treatment fluid (e.g. perfusion fluid) is generally a physiological salt solution with one or a cocktail of active ingredients, such as drugs and pharmaceutics. Because the device of the present invention is preferably devised to become positioned percutaneously, no surgery is needed, thereby avoiding a lot of stress on the body of the patient. Furthermore, treatment as such can be repeated more times and with smaller time intervals, even on patients in a lesser condition. After each treatment session the delivery device and all accessories can be retrieved. By isolating the organ during perfusion significantly higher doses of active ingredient can be used, thereby improving effectiveness while decreasing side effects, resulting in enhancing the quality of the patients live during and after treatment.

Figure 1:
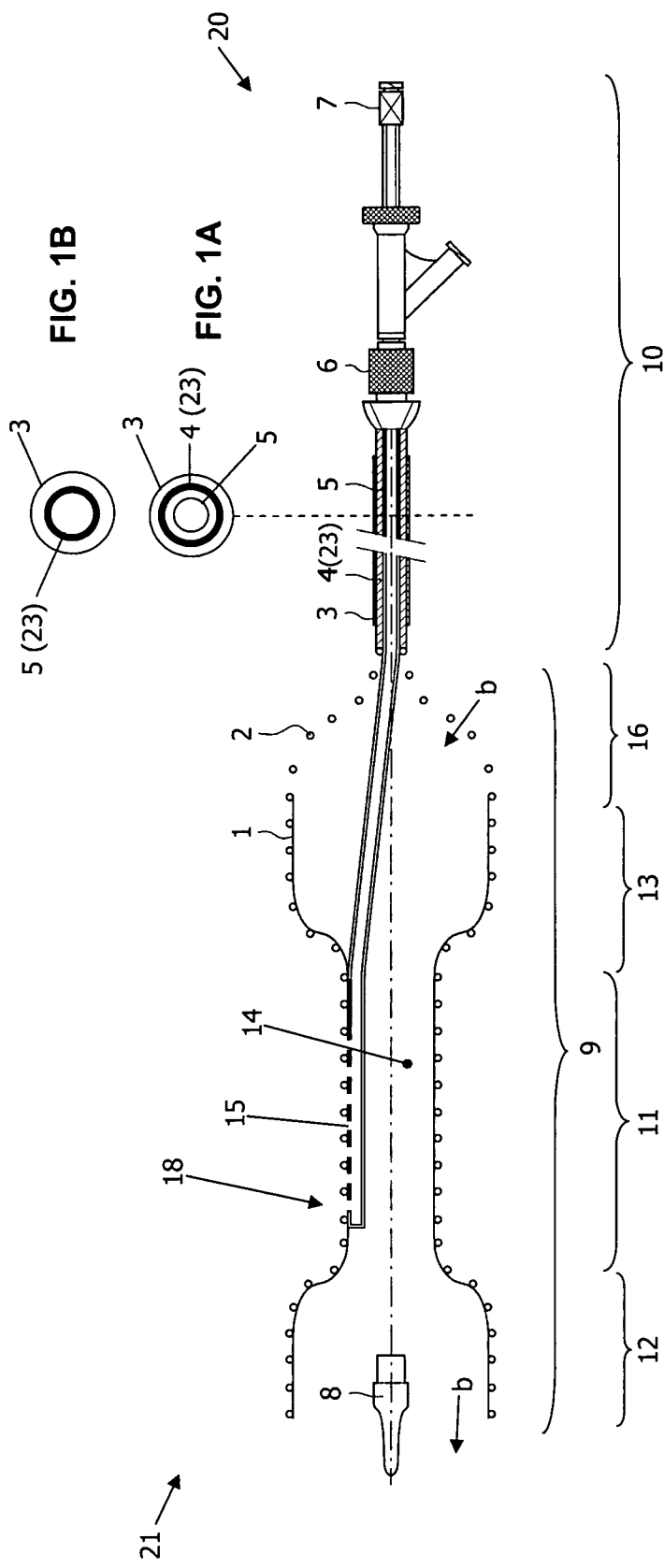
FIG. 1 illustrates a device of the present invention in the expanded state comprising a tubular member (dumb-bell shaped) attached to a catheter.

FIG. 1 illustrates an embodiment of the medical delivery device according to the present invention. The device comprises a radially, self-expandable tubular member 9, shown in the expanded state attached to a delivery catheter 10. FIG. 1A shows a transverse cross-section of the catheter.

One embodiment of the present invention is medical device for the delivery of medical treatment fluid to a body vessel, having a distal 21 and a proximal 20 end, comprising a hollow, self-expanding tubular member 9 and a delivery catheter 10 suitable for deploying a self-expanding tubular member 9, wherein:

the tubular member 9 is configured to expand radially to form a central part 11 flanked by two annular ridges—a distal annular ridge 12 and a proximal annular ridge 13, the tubular member 9 comprises a liquid-impermeable area, defined at least by the region flanked by the annular ridges 12,13, the tubular member 9 comprises two liquid-permeable regions, one distal to the distal annular ridge 12 and one proximal to the proximal annular ridge 13, so forming a passageway 14 between the distal end 21 and the proximal end 20 of the tubular member 9 for the flow of vessel fluid, the proximal end 20 of the tubular member 9 is attached to the distal end 21 of the delivery catheter 10, the liquid impermeable area is disposed with one or more fluid ports 15 for the passage of treatment fluid.

The self-expandable tubular member 9 (known herein as 'tubular member') is typically an elastic tube that self-expands after having been compacted. Illustrative examples of self-expandable tubular members are disclosed in the following documents all of which are incorporated herein by reference: U.S. Pat. No. 5,876,445, U.S. Pat. No. 5,366,504, U.S. Pat. No. 5,234,457, U.S. Pat. No. 5,061,275; Watkinson et al. The role of self-expanding metallic endoprostheses in esophageal structures, "*Seminars in Interventional Radiology*", 13(1):17-26 (March 1996).

The tubular member 9 comprises, in the expanded state, a central part 11 flanked by two annular ridges—a proximal annular ridge 13 and a distal annular ridge 12. The central part 11 radially expands to a lesser degree compared to the annular ridges 12, 13. The expanded central part 11 typically has a cylindrical shape while the annular ridges 12, 13 are at least partly conical, so forming a funnel-like structure in the expanded state. By designing the device as such, it is formed partly as an hour-glass or dumb-bell upon expansion. When deployed in a bodily vessel, the central part 11 forms an annular lumen 18, sealed by the annular ridges 12, 13 for the delivery of a liquid, such as a medicament-containing fluid.

The skilled person will appreciate the diameters of the tubular member 9 at the annular ridges 12, 13 and central part 11 in the expanded state may be adapted according to the diameter of the vessel at the deployment site. The diameter of the central part 11 should be wide enough to avoid obstruction of blood flow, but not too wide that flow reaches high levels that will affect leakage resistance and disturb laminar flow.

The minimum diameter of the central part 11 in the expanded state may be 45, 50, 55, 60, 65, 70, 76, 80, 85, 90, or 95% of the internal diameter of the vena cava, or a value between any two of the aforementioned values. Preferably the minimum diameter of the central part 11 in the expanded state is at least 50% of internal diameter of the vena cava. According to one aspect of the invention, the minimum diameter of the central part 11 in the expanded state is between 6, 8, 10, 12, 14, 16, 18, 20, 22 mm or a value in the range between any two of the aforementioned values, preferably 8 to 18 mm diameter.

The maximum diameter of the annular ridges 12, 13 in the expanded state may be 5, 10, 15, 20, 25, 30, or 35% larger than the internal diameter of the vena cava, or a value between any two of the aforementioned values. Preferably the maximum diameter of the annular ridges 12, 13 in the expanded state is between 10, 15, 20, 25, 30% larger than internal diameter of the vena cava. According to one aspect of the invention, the maximum diameter of the annular ridges 12, 13 in the expanded state is between 20, 25, 30, 35, 40, 45 mm or a value in the range between any two of the aforementioned values, preferably 20, 26, 33 or 43 mm diameter.

According to one aspect of the invention, the difference between the maximum diameters of the annular ridges 12, 13 and the minimum diameter of the central part 11 in the expanded state may be 2, 3, 4, 5 or 6 mm or a value in the range between any two of the aforementioned values, preferably 4 to 5 mm diameter.

The region flanked by the annular ridges 12, 13 defines a liquid impermeable area. The skilled person will understand the adaptations to the tubular member 9 necessary to define a liquid-impermeable area that provide sealed annular lumen 18 in the deployed state. Generally, the liquid-impermeable area will extend between the annular ridges 12, 13, from the region of maximum diameter of the proximal annular ridge 13 to the region of maximum diameter of the distal annular ridge 12. It is within the practices of the skilled person to determine a lesser or greater area, for example, depending on the patency of the vessel wall.

Through the inner part of the tubular member extends a passageway 14 between the distal end 21 and the proximal end 20 of the tubular member 9; fluid is able to flow therebetween. The tubular member 9 comprises two liquid-permeable areas, one distal to the distal annular ridge 12 and one proximal to the proximal annular ridge 13, so fluid can flow from through the passageway from the distal end 21 and the proximal end 20 or vice versa. Preferably, the liquid-permeable region 16 of the distal end 21 of the tubular member 9 comprises an open-mouthed region, while the liquid-permeable region of the proximal end 20 comprises a region 16 devoid of liquid-impermeable lining.

According to one aspect of the invention the tubular member 9 comprises a carrier 2 and a liquid-impermeable liner 1. The carrier part 2 is typically, though not always, the outmost part of the device, and contacts the vessel wall in the deployed state. The carrier 2 expands in the manner mentioned above. The carrier 2 is preferably retractable which means that it normally adopts the hour-glass or dumb-bell shape mentioned above; when retracted into a cylindrical sheath, the carrier can be compressed to adopt an essentially cylindrical state, suitable for introduction into and freely positioning within a vessel. The carrier 2 can be described as being self-expanding. The carrier is attached to the catheter, to a pusher means 23 element therein described below. Preferably, the proximal end 20 of the carrier 2 is attached circumferentially to the distal end 21 of the pusher means 23, so giving the proximal end 20 of the tubular member 9 a conical shape 16.

The tubular member 9 or carrier 2 is attached to the catheter 10 or pusher means 23. It is configured to remain attached when the tubular member 9 or carrier 2 is in the retracted and deployed position. According to one aspect of the invention, it is non-releasably attached, meaning that the member 9 or carrier 2 cannot be released, in situ, from the catheter 10 or pusher means 23. In other words, the device may be devoid of a mechanism for releasing the tubular member in situ. This feature allows the tubular member to be withdrawn at the same time as the catheter, without the possibility of leaving the tubular member in the vessel. A non-releasable attachment may still allow the member 9 or carrier 2, to be unattached from catheter 10 or pusher means 23 outside by the body, for example, using a screw fitting, a clip, a push fitting or any other secure coupling. A non-releasable attachment would also include the possibility that the member 9 or carrier 2, is permanently attached to the catheter 10 or pusher means 23.

In the expanded state, the carrier is able to retain its shape without the requirement for an additional source of pressure, for example, from a balloon catheter. The carrier 2 may or may not maintain an essentially constant axial length in the compressed state compared with the expanded state.

The carrier part 2 is preferably made of a braided wire mesh, woven so as to self-expand radially. In an embodiment, the carrier is made from a surgical wire preferably of an alloy comprising Cobalt, Chromium, Nickel, Molybdenum and Iron, and more preferably a surgical wire in accordance to the standard ASTM F 1058. Alternatively, the carrier part 2 may be a knitted mesh of nitinol wire flexible in both the radial and longitudinal axes. Alternatively, other materials, such as shape memory alloy or synthetic material, can be used to produce the carrier. The carrier part 2 may, alternatively, be laser cut. The shape of the central part 11 may be formed by using crimping or heat treatment. The carrier may show a high degree of flexibility and a radial force that assures a good contact with the vessel wall after positioning. The carrier part 2 is liquid permeable, which means that fluid can flow therethrough, without substantial hindrance. This is achieved in the carrier because it is formed from an open wire structure and may comprise an open mouthed end. A liquid permeable region may comprise one or more openings, at least wide enough to avoid capillary action though the opening.

Because the carrier part 2 is preferably formed from an open mesh structure, it contacts the vessel wall securely in the expanded state, owing to the open structure, creating a plurality of friction points. In an expanded state, the device is securely anchored and provides strong sealing against the vessel wall. There is no requirement for applying additional pressure to the vessel walls, for example, from a balloon.

Another component of the tubular member 9 is the liner 1, which is made from a liquid-impermeable material. This is typically attached partly to the walls of the carrier, inside or outside the passageway lumen 14 of the device. The liner 1 is disposed at least in the region of the annular lumen 18, so that the passageway lumen 14 is liquid-sealed from the annular lumen 18 in the deployed state. Preferably the liner 1 is disposed in an area defined at least by the region flanked by the annular ridges 12, 13.

The liner 1 may be made from a biocompatible material, preferentially a medical grade expandable material e.g. an elastic material which can expand at the same time as the carrier 2. The liner may be made from a medical grade polycarbonate polyurethane formulation. The liner may, alternatively, be made from polytetrafluoroethylene, polyurethane, silicone or polyethylene terephthalate polymers. The most preferred materials are indicated in Table 1 below:

TABLE 1

Examples of preferred liner materials for use in the present invention. All brand names are registered trademarks.

| | Supplier | Brand name | Elastomer |
|---|---|---|---|
| 1 | Polymer Technology Group Inc, Berkeley CA, USA (Licensed by Boston Scientific) | Bionate (Corethane) | Thermoplastic Polycarbonate Urethane |
| 2 | B. F. Goodrich, Cleveland OH, USA | Estane | Thermoplastic Polyester Urethane |
| 3 | Thermedics Inc, Woburn MA, USA | Tecoflex | Thermoplastic Polyether Urethanes |
| 4 | CT Biomaterials, Woburn USA | Chronoflex | Thermoplastic Aromatic Polycarbonate Polyurethane |
| 5 | Aortech, Sidney, Aus | Elasteon | Siloxane based Macrodiol, Aromatic Polyurethane |

The liner 1 may be attached to the carrier 2 by chemical or thermal bonding. The liquid-impermeable area formed by the liner 1 is disposed with one or more fluid ports 15 for the passage of treatment fluid; this is described in more detail further below.

Through the inner part of the tubular member extends a passageway 14 between the distal end 21 and the proximal end 20 of the tubular member 9; fluid is able to flow therebetween. The tubular member 9 comprises at least two liquid-permeable areas, one distal to the distal annular ridge 12 and one proximal to the proximal annular ridge 13, so fluid can flow from through the passageway 14 from the distal end 21 and the proximal end 20 or vice versa. A flow is indicate by arrows 'b' in FIG. 1. The skilled person will realize that liquid permeable areas should not extend into the liquid impermeable region so that the seal of the annular lumen 18 is breached. Preferably, the distal end 21 of the tubular member is open-mouthed, while the proximal end 20 is closed but is disposed with a liquid-permeable region 16 i.e. a region devoid of liner 1.

According to one aspect of the invention, a region of the carrier 16 towards the proximal end 20 of the proximal annular ridge 13, is devoid of liner 1. According to another aspect of the invention, at least part of the carrier 2 between the distal end 21 of the catheter 10 and proximal end 20 of the proximal annular ridge 13 is devoid of liner 1. This creates a large liquid passageway 14 inside the tubular member 9 while the catheter 10 is still attached. This configuration has advantages over conventional designs which employ openings and lumens within the narrow confines of the catheter tube to maintain the flow of blood. Conventional lumens are narrow bore, and can cause the build up of pressure towards the proximal side of the occlusion device. Known devices thus require catheter tubing having larger diameters to accommodate wider a blood lumen, which catheters can then be difficult to navigate along a tortuous path of a blood vessel for example. The present device, by contrast, dispenses with a catheter blood lumen, and maintains blood flow using a wide bore passageway in the expanding tubular member 9, and with a narrow diameter catheter.

The delivery catheter 10 part of the device is used to introduce and guide the tubular member 9 into the body vessel. The delivery catheter 10 is also used to restrain, temporarily, the tubular member 9 in a compressed state at the distal end of the catheter. It is also used to deliver liquid to and/or from the annular lumen 18. In use, the catheter is introduced to a desired site within a body vessel, the restraint is removed, thereby allowing the tubular member 9 to expand by its own elastic and apply sealing pressure to the vessel wall using the annular ridges 12, 13.

Examples of delivery systems for expandable tubular members are described in the following US patents which are all incorporated herein by reference: U.S. Pat. No. 5,484,444, U.S. Pat. No. 4,990,151, and U.S. Pat. No. 4,732,152.

According to one embodiment of the invention, the catheter comprises an outer tubing 3, pusher means 23 for deployment of the tubular member 9, and an inner tube 5, which extend along the length of the catheter. The pusher means 23 may be a pusher rod (or stick) 4 at least partly co-axially or concentrically disposed around the inner tube 5 (FIG. 1A). Alternatively, the pusher means 23 may be formed from the wall of the inner tube 5 (FIG. 1B). The outer tubing 3 may be coaxially or concentrically disposed around the pusher rod 4. Where the pusher means 23 is formed from the wall of the inner tube 5, the outer tubing 3 may be coaxially or concentrically disposed around the inner tube 5. The pusher means 23 is configured to translate axially along the length of the catheter, relative to the outer tubing 3. Where the pusher means 23 is formed of the wall of the inner tube 5, the inner tube 5 may be configured to translate axially along the length catheter, relative to the outer tubing 3. Movement of the pusher means 23 may be effected by operating a plunger 7 mechanically connected to the pusher rod 5 or inner tubing 5, at the proximal end 20 of the catheter 10. The position of the outer tubing 3 may be maintained or adjusted using a grip area 6. The distal end 21 of pusher means 23 is mechanically attached to the proximal end of the carrier 2.

According to one embodiment of the invention, the catheter 10 comprises, (a) an inner tube 5; (b) an outer tube 3, (c) a pusher means 23, said outer tube 3 surrounding at least a portion of the length of said inner tube 5. Said pusher rod 4 may be disposed between said inner tube 5 and said outer tube 3. Alternatively, the pusher means 23 may be formed of the wall of the inner tube 5, in which case the outer tube 3 surrounds at least a portion of the length of said inner tube 5 whose wall forms the pusher means 23. The pusher rod 4 is adapted for axial movement relative to said outer tube. The tubular member 9 is attached to the distal end of the pusher means 23, and may be retracted in the outer tube 3 in the compressed state.

Figure 2:
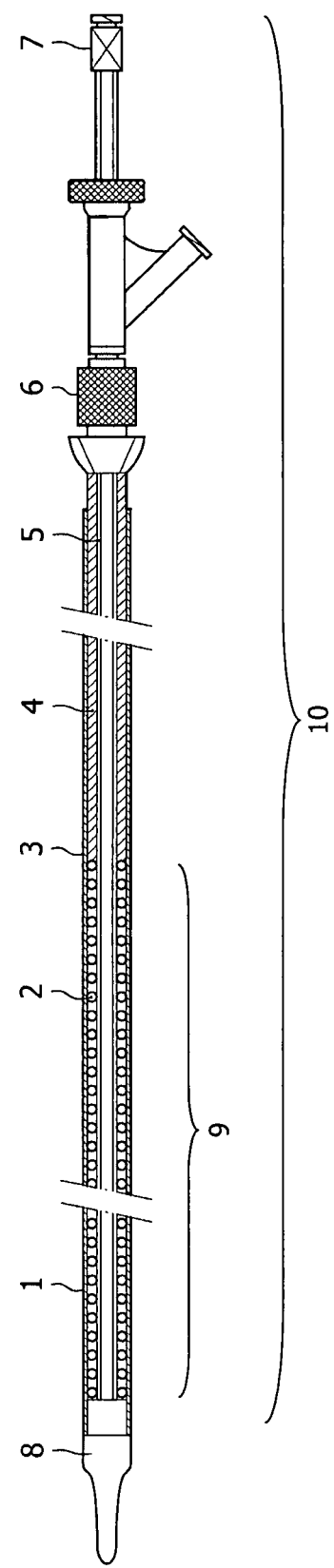
FIG. 2 illustrates the device of FIG. 1 where the tubular member is in its collapsed, compressed state.

FIG. 2 illustrates the tubular member 9, comprising the liner 1 and carrier 2, retracted within the outer tubing 3 of the catheter 10. In the compressed state, the tubular member 9 is maintained compressed by inner surface of the outer tube 3, which acts as a restraint.

According to one aspect of the invention, the catheter further comprises a restraining member disposed between said outer tube 3 and tubular member 9, said restraining member being dimensioned to maintain said tubular member 9 in a compressed state.

The aforementioned restraining member may be a braided tube (or any other type of tube) surrounding said tubular member 9, said braided tube preferably being made from a strong, flexible, filamentary material having a low coefficient of friction. Examples of such materials may be a fine polyester or metal wire. The braided tube may be formed directly over the tubular member 9, preferably using an automated braiding machine, or may be pre-formed and then inserted over the tubular member 9. Where the braided tube is pre-formed and inserted over the tubular member 9, the system preferably further includes a braid holding sleeve secured to the inner tube 5, said braid holding sleeve being adapted to receive the proximal end of the braided tube. The distal end of the restraining member is preferably mechanically coupled to the distal end of the outer tube 3 so that retraction of the outer tube 3 causes the restraining member to retract from the tubular member 9, thereby allowing the tubular member 9 to self-expand.

The catheter 10, and tubular member 9 may be inserted in a blood vessel and, preferably with the aid of a guide wire, manoeuvred to its desired position. The guidewire may be disposed with a separate guidewire lumen. Alternatively, the inner tube 5 may act as a guidewire lumen. The guide wire may be that positioned through the liver to the portal vein to guide a portal vein device. The tubular member 9 may be deployed by moving the pusher means 23 axially in the distal direction, while the outer tubing 3 is held in a fixed position. Preferably, the tubular member 9 is deployed by retracting the outer tubing 3 axially in the proximal direction while the pusher means 23 is held in a fixed position. The practitioner may position the tubular member appropriately to account for any shortening of the device during deployment. As the restraint of the outer tubing is removed, the tubular member 9 self-expands. The catheter may optionally be closed with a tip 8.

As seen in FIG. 1 the device comprising the liner 1 and carrier 2 expands to its dumb-bell or hour-glass shape. Retrieval of the device after treatment is by withdrawing the tubular member 9 into the outer tubing 3. This may be achieved by drawing the pusher means 23 towards the proximal end 20 while maintaining the position of the outer tubing 3. Alternatively, the outer tubing 3 may be pushed towards the distal end 21 while maintaining the position of the pusher rod 4. Because the carrier 2 is connected to the pusher means 23, the tubular member 9 is forced to take its non-expanded state inside the outer tubing 3 again. The device can then be carefully withdrawn from the blood vessel.

The inner tube 5 of the catheter 10 is in fluid connection with the one or more ports 15 present in the wall tubular member 9. Said port 15 is disposed in the wall of the tubular member 9 in the region of the annular lumen 18. The port 15 may be disposed in the central part 11, and/or in the parts of the annular ridges 12, 13 that form the annular lumen 18. The port 15 allows the lumen of the inner tube 5 to be in fluid contact with the annular lumen 18 so that liquids (e.g. perfusion fluid) can be passed along the catheter 10, to and/or from the annular lumen 18. The port 15 may also act as an entry/exit point for a guidewire.

The skilled person will understand that the connection between the inner tube 5 and the ports 15 can be optimised so that expansion of the tubular member 9 does not result in axial tension in the inner tube 5, or excessive slack along the inner tube 5. According to one embodiment of the invention, the inner tube 5 of the catheter 10 extends from the outer tubing 3 and is in fluid connection with the annular lumen 18 via one or more ports 15. In other words, the inner tube 5 may extend from the outer tubing 3 to connect with the ports 15, as a continuous extension of the inner tube. According to another embodiment of the invention, the inner tube 5 of the catheter 10 is in fluid connection with a port 15 of the tubular member 9 using a bridging tubing 19.

FIG. 5. shows one configuration of the inner tube 5 whereby a rigid bridging tube 19 is employed to connect fluidicly a port 15 of the tubular member 9 to the inner tube 5 of the catheter 10. FIG. 6. shows an alternative configuration of the inner tube 5 whereby an axially expandable bridging tube 19' is employed to connect fluidicly a port 15 of the tubular member 9 to the inner tube 5 of the catheter 10. The latter bridging tubing 19' is typically made from a flexible material which can expand by virtue of elastic properties and/or by use of a concertina-like folding of the unexpanded bridging tube 19'.

Figure 3A:
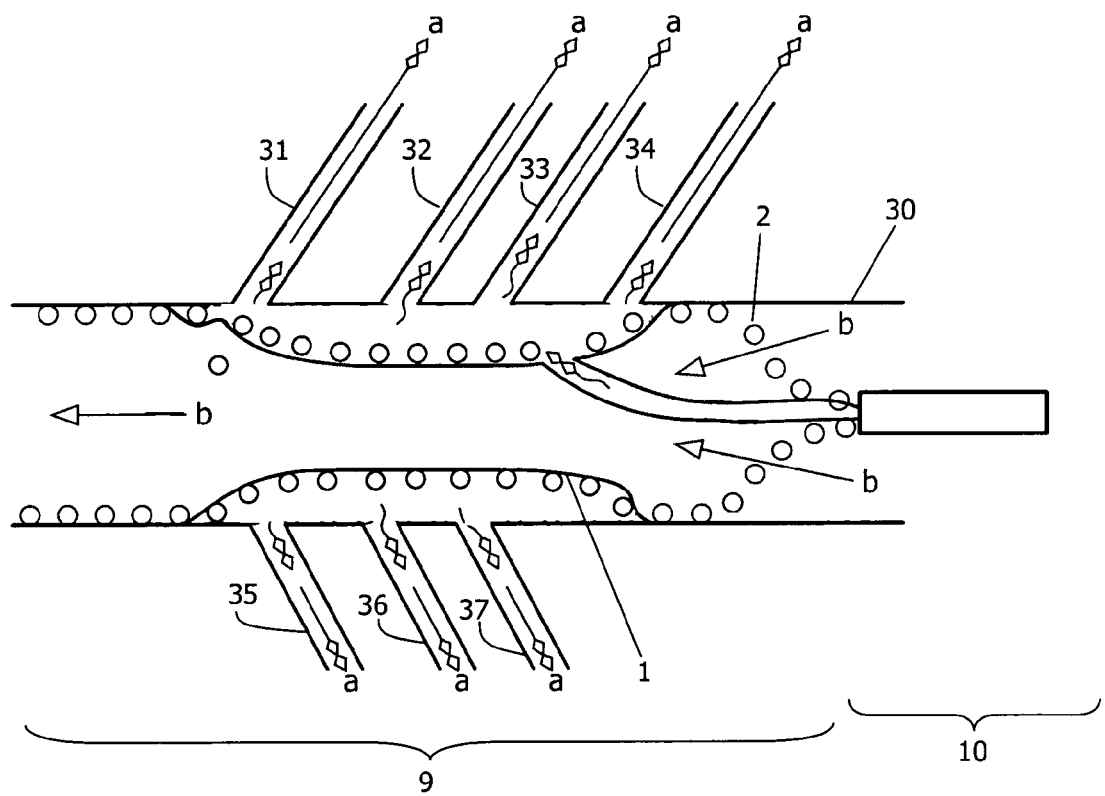
Figure 3B:
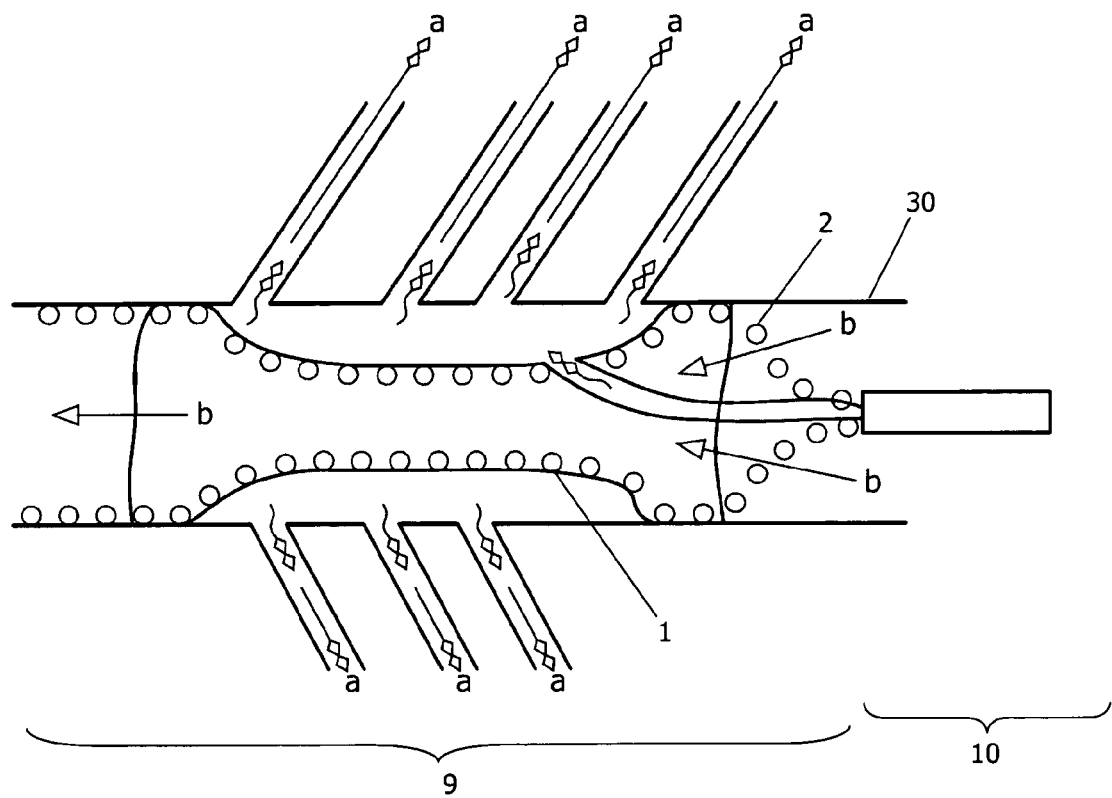

FIGS. 3A and 3B illustrate the system where the tubular member 9 is deployed within a vessel 30. The proximal 13 and distal 12 annular ridges contact the wall of the vessel 30, and the central part 11 forms an annular lumen 18. Blood (b) is able to flow freely through the unlined portion of the tubular member 9. Fluid (a), such as perfusion fluid may be introduced to or pumped from the annular lumen 18 inner tube 5 along the inner tube 5. The annular lumen 18 may span the region of branched vessels 31 to 37, which can be treated with treatment fluid.

In FIG. 3A, the liner 1 is attached to the carrier 2 such that the liner is on the inside of the carrier 2. FIG. 3B shows an alternative configuration whereby the liner 1 is on the outside of the carrier 2.

The device as described above is particularly useful for the minimal invasive and repeatable perfusion of an organ. After positioning, as mentioned, before the device expands to achieve its dumb-bell or hour-glass shape. The proximal annular ridge 13 and distal annular ridge 12 (i.e. the end parts of the device) expand until they press against the inner wall of the vessel, thereby fixing the device at the selected position and providing a liquid tight seal inside the vessel. The central part 11 of the device expands to a lesser degree, thereby creating an annular lumen 18 between the device and the inner wall of the vessel. Inside the device is a passageway lumen 14 for bypassing the systemic blood past the sealed area. This way the passageway lumen 14 defines a new blood path to allow the continuation of the systemic blood flow during perfusion. The liquid tight sealing of the vessel by the proximal annular ridge 13 and distal annular ridge 12 and the liquid tight liner 1 of the device form a liquid tight barrier, separating the systemic blood flowing through the passageway 14 from the blood and/or liquid present in the annular lumen 18. This way perfusion fluid can be delivered to the annular lumen 18 in contact with the organ to be perfused, while minimizing the risk of leaking perfusion fluid into the systemic blood flow. The perfusion fluid is delivered to the cavity by a delivery catheter, fixed to the device and thereby positioned together with the device, or connected to the flush opening in the device after expansion.

Although the following describes the use of this system in a retrograde liver perfusion application, the application is only exemplifying. It is clear to a person skilled in the art that this system can also be used for isolating and perfusing other organs than the liver. Furthermore, this system can also be used in antegrade as well as in retrograde perfusion. Furthermore, it can be used to deliver treatment fluid locally to the wall of a vessel.

The present invention makes use of occluding three main blood vessels connected to the liver—the vena porta (VP, hepatic portal vein), hepatic artery (HA) and hepatic vein (HV) to achieve site specific perfusion. Depending on the type and positioning of the cells for treatment (e.g. cancer cells), the practitioner can decide which vessel to apply perfusion fluid to, and which vessel to drain it from.

In one aspect, perfusion may proceed using the present device, inserted in the inferior vena cava, to occlude the hepatic vein (HV), and provide a perfusion passage along the hepatic vein. A second occlusion device (e.g. balloon device) to occlude and optionally perfuse the vena porta (VP) is fitted, and a third occlusion device (e.g. balloon device) to occlude and optionally perfuse the hepatic artery (HA) is fitted. Additionally, the VP device may serve as a shunt for the blood coming from the intestines.

The practitioner has several options available as to the flow of perfusion fluid when the three occlusion devices are fitted.

According to one aspect of the invention, perfusion fluid may be pumped from the present device, along the HV towards the liver; the perfusion fluid may be drained from the liver along the VP passage towards the second (VP) occlusion device, fitted with a perfusion means. Alternatively, perfusion fluid may be pumped from the second (VP) occlusion device towards the liver along the VP passage, and drained from the liver along the HV passage towards the present device.

According to another aspect of the invention, perfusion fluid may be pumped from the present device, along the HV towards the liver; the perfusion fluid may be drained from the liver along the HA passage towards the third (HA) occlusion device fitted with a perfusion means. Alternatively, perfusion fluid may be pumped from the third (HA) occlusion device towards the liver along the HA passage, and drained from the liver along the HV passage towards the present device.

For isolation and perfusion of the liver, the expandable part of the device is inserted into the inferior vena cava using the integrated catheter, thereby blocking the flow from the HVs into the vena cava.

A second catheter is placed in the VP by means of an introducer. This introducer comprises a perfusion lumen, while the catheter has a bypass lumen and an occlusive seal, preferably a balloon. The VP catheter may be provided with a perfusion port and associated tubing. The seal is placed upstream of the veins into which the VP branches before entering the liver. Due to its position between the liver and the intestinal parts, the VP is difficult to enter. Therefore, the VP can be entered through the liver as practiced for the placement of a Transjugular Intrahepatic Portosystemic Shunt as is commonly understood by one of skill in the art. Another way to position a similar device in the vena porta is by direct needling.

A third catheter is placed in the HA. Said catheter has an occlusive seal, preferably a balloon, for further isolating the liver. It may be provided with a perfusion port and associated tubing. Insertion of said catheter occurs via the right femoralis artery into the hepatic communis artery.

According to one aspect of the invention, a bypass circuit is formed by connecting the annular lumen 18 of the present invention to the perfusion port of the second (VP) catheter by means of a bypass pump. Perfusion fluid can then flow across the liver, between the HV and VP. According to one aspect of the invention the partially extra-corporeal bypass circuit is formed by connecting the proximal end opening of the bypass lumen of said second (VP) catheter to the annular lumen 18 of the present invention via the inner tubing 5, by means of a bypass pump, e.g. a roller pump or a centrifugal pump. In the bypass circuit the blood of the digestive system and its associated glands may be taken out of circulation through the lumen of the second catheter and re-entered into the systemic blood circulation. Furthermore, a scintillation counter is preferably connected to the extracorporeal part of this circuit for detecting a possible leakage of perfusion fluid.

Also, a partially extra-corporeal perfusion circuit may be formed by connecting the proximal end opening of the perfusion lumen of said introducer of the second catheter to a perfusion fluid reservoir by means for establishing a negative relative pressure in the liver, e.g. a pump such as a roller pump or centrifugal pump. The annular lumen 18 may also be connected, via the inner tubing 5 to the reservoir via a pump. This reservoir is a container for the perfusion fluid, but serves also as a manifold for receiving tubes with blood, active ingredients and other additions. The pump can be a pump such as e.g. a roller pump or centrifugal pump, but frequently a heart lung machine is used. Furthermore, filters, temperature regulators, oxygenerators and/or other equipment are preferably connected to the perfusion fluid circuit. In this circuit the perfusion fluid is pumped from the vena porta into the reservoir and further into the isolated cavity in the vena cava, allowing isolated perfusion of the liver. Radioactive labeled material can be brought into this perfusion circuit for allowing detection of leakage by the scintillation counter described before.

The perfusion circuit can have a reservoir or manifold with one or more reservoirs that may comprise a means for drawing medicament or perfusion fluid into the circuit. The circuit may permit entry to the circuit through one or more connectors. The connectors may be unique or specific to particular medicine containers. These connectors can permit sterile connection of the medicine container/reservoir with the perfusion circuit. Advantages of such a connection system includes:

a. Assures sterility in a potentially unsterile environment,
b. Resistance to mechanical stresses for the duration of the perfusion treatment (e.g. 60 minutes) with conscious patients,
c. Prevents misuse with non-authorised drugs or concentrations of drugs,
d. Positive patient identification and relation to patient specific drug preparation/the reservoir can have an identification code label or connector.
e. Such a positive identification can also be used to enter control parameters for treatment with automated control systems to measure and steer for instance perfusion flow, pressure, temperature, time, drug (concentrations), sequential drug additions. Etc.

The VP is advantageous to use for establishing a negative relative pressure at the perfusion outlet of the liver, since it is surrounded and strengthened by a relatively rigid structure that prevents the vena porta from collapsing. In embodiments of the invention when this feature does not occur in the vessels entering or leaving the organ to be perfused, it is conceivable to provide, at the perfusion outlet opening of the catheter, a structure devised to prevent the vessel from collapsing, e.g. in the form of a stent. This reinforcement of the vessel is needed because an increase in pressure and amount of perfusion fluid results in an increase in the leakage and thereby an increase of the amount perfusion fluid entering into and contaminating the systemic blood circulation.

The above embodiments describe a bypass circuit between the HV and VP using a device of the present invention. Using the teachings herein, the skilled person can equally apply the invention and methods to create a bypass circuit between the HV and HA using a device of the present invention.

The extra-corporeal parts of the bypass and perfusion circuits consist mainly of tubing, which is connected to the proximal ends of the catheters through per se known connections. These connections can be luer lock or screw connections, but also other types of connections are conceivable.

Perfusion fluids to be used during perfusion of the liver or another organ are entered into the perfusion circuit through the perfusion fluid reservoir or by infusing into a branch of an inlet catheter. For this purpose the delivery catheter of the perfusion system is preferred, and the perfusion fluid can be infused directly into the isolated cavity in the vena cava, created by the expanded device of the perfusion system.

One aspect of the present invention is device of the present invention for minimal invasive and repeatable organ perfusion of a living being by positioning the device into the inferior vena cava, thereby:
a. blocking the flow path of blood in the inferior vena cava;
b. providing a flow path for the blood through the passageway 14 of the device;
c. creating an isolated cavity (annular lumen) 18 between the medical device and the wall of the vena cava, which is in contact with the liver by the hepatic veins; and
d. delivering the perfusion fluid to or from this cavity by means of the delivery catheter.

As will be clear to a person skilled in the art, this is only one possible way of isolating and perfusing the liver. A second possibility comprises placing the occlusive seal in the vena porta while positioning the catheter with bypass lumen and occlusive seal in the hepatic artery.

One possible device according to the invention is explained above; the following describes four other systems for minimally invasive isolation and perfusion of an organ, without the need for surgery.

The first of these four systems, hereafter called the second system, is illustrated in FIG. 4B and comprises an expandable medical device and a delivery catheter. This second system strongly resembles the first system, depicted in FIG. 4A and described before. The device of the second system also has a dumb-bell or hour-glass shape, provided for by the radially expandable tubular member wherein the ends expand to a higher degree than the central part. The delivery catheter however is formed as a needle and delivers the perfusion fluid by puncturing the wall of the expanded device.

The device of the second system is further characterized in that it is formed by at least a carrier and a liquid tight liner, exhibiting the same features as the carrier and liner of the first system. Additional to these features, the liner has to remain liquid tight even after puncturing by the needle shaped catheter. As described for the first system, the carrier of the second system can be connected to and support only the ends or the entire length of the liner, thereby forming the dumb-bell or hour-glass shape.

The positioning of the second system also occurs by using a positioning device. The non-expanded carrier, mounted on a stick, and the liner are integrated in between an outer tubing and inner lumen. The delivery catheter formed as a needle can be integrated in the positioning device, and preferably as the inner lumen, or can become inserted after positioning of the expandable device. The positioning device closed with a tip can become inserted in a blood vessel and, preferably with the aid of a guide wire, manoeuvred to its selected position. When arrived, the device is expanded to its dumb-bell or hour-glass shape after the outer tube is retracted by slowly pulling it while the inner tube is held in a fixed position. The delivery catheter, present in the positioning device, preferably as inner tube, or inserted after positioning of the expandable device, is placed by puncturing the liner. This system can be retrieved after perfusion by holding the inner tube in a fixed position and slowly pushing the outer tube over the device, thereby forcing the latter to take its non-expanded state in the positioning device again. The system can then be carefully withdrawn from the blood vessel. Obviously, the delivery catheter can also be removed before retrieval of the expandable device.

As the first system, the second system is devised to allow minimally invasive isolation and perfusion of an organ without the need for surgery. The expanded end parts of the dumb-bell or hour-glass shaped device provide a liquid tight seal inside a vessel by pressing themselves against its inner wall. The central part of the expanded device creates a cavity between the device and the inner wall of the vessel. Continuation of the systemic blood flow is provided for by a lumen through the device, defining a new flow path during perfusion. This systemic blood flow is separated from the blood and/or fluid in said cavity by a liquid tight barrier, formed by the liquid tight sealing of the vessel by the end parts and the liquid tight liner of the device. This way perfusion fluid can be delivered to this cavity in contact with the organ to be perfused, while minimizing the risk of leaking perfusion fluid into the systemic blood flow. Delivery of the perfusion fluid into the cavity is achieved by a needle shaped catheter after puncturing of the liner.

The third system, illustrated in FIG. 4C, comprises a tube and three or more expandable balloons or cylinders. The tube has a flush opening and is closed at its distal end. The balloons or cylinders are placed at or near the distal end and connected to the outside of the tube. Furthermore, as can be seen in FIG. 4C, they are placed at different sides around the tube and in the same direction as the tube, i.e. longitudinally. The balloons or cylinders around the flush opening are also connected to each other at their extremities.

The components of the third system have to be made of a biocompatible material or materials. The tube is further specified as being liquid impermeable. Expansion of the balloons is achieved by inflation while the cylinders are provided with a shape memory, thereby promoting expansion after release. The balloons or cylinders further have to exhibit a high degree of flexibility and a radial force assuring a good contact with the vessel wall after positioning. The balloons or cylinders around the flush opening also have to be liquid tight in order to form, together with the tube, the liquid tight barrier of the system enclosing an isolated cavity.

Positioning of the third system executed with cylinders occurs by using a positioning device. The system becomes integrated inside the outer tube of the positioning device with the cylinders, mounted on a stick, in the non-expanded state. The loaded positioning device can then be inserted into a blood vessel and, preferably with the aid of a guide wire, manoeuvred to its selected position. There the outer tube is retracted by slowly pulling the outer tube while the tube of the perfusion system is held in a fixed position. Removal of the outer tube results in expansion of the cylinders, thereby fixating the system at that position. Retrieval of the system is achieved by holding the tube of the system in a fixed position while pushing the outer tube carefully over the system and withdrawn the whole from the blood vessel. A system with balloons can be delivered the same way, or can be configured in such that no positioning device is needed. This way, the third system is inserted in a blood vessel and manoeuvred, preferably aided with a guide wire, to its desired position. Arrived there the balloons become inflated to fixate the system at its position. After perfusion, the balloons are deflated and the system can be withdrawn from the blood vessel.

The third system described above can be used for minimally invasive isolation and perfusion of an organ. After positioning as mentioned before, the balloons or cylinders are expanded, thereby fixating the system at its position. In between the balloons or cylinders, the tube and the wall of the blood vessel longitudinal paths are created for continuation of the systemic blood flow. At the same time the balloons or cylinders around the flush opening, which are connected to each other by their extremities, provide a cavity in contact with the organ to be perfused and isolated from said systemic blood flow. The perfusion fluid is guided through the tube of the system and is brought inside the cavity through the flush opening, allowing isolated perfusion of the organ.

The fourth system, illustrated in FIG. 4D, comprises one or more tubes and a stent. The tubes as well as the wall of the stent are liquid impermeable. Furthermore, they have to be made out of a biocompatible material or materials. The stent can be self- or balloon expandable and has a high degree of flexibility and a radial force assuring a good contact with the vessel wall after positioning.

Positioning of the fourth system occurs in two steps. The first step consists of positioning the tube or tubes. Therefore, the tube or tubes are guided through a blood vessel adjacent to main input and/or output vessels of the organ to be perfused and the distal end of each tube is placed in one of these input and/or output vessels. Optionally an expandable seal, such as a balloon, is provided at the distal end of each tube, thereby securing the tube in and sealing said vessel after positioning. In the second step, the stent is positioned in the adjacent blood vessel in such that it presses the tube or tubes into the wall of said blood vessel. For positioning of the stent a positioning device is used, integrating the non-expanded stent, preferably mounted on a stick, between its outer and its inner tube. The loaded positioning device can then be inserted into a blood vessel and, preferably with the aid of a guide wire, manoeuvred to its selected position. There the outer tube is retracted by slowly pulling the outer tube while the inner tube is held in a fixed position. Removal of the outer tube results in expansion of the stent, thereby fixating the system at that position. Retrieval of the system is achieved by holding the inner tube in a fixed position while pushing the outer tube carefully over the stent and withdrawn the whole from the blood vessel.

The fourth system, as described above, is especially designed for minimally invasive isolation and perfusion of an organ. The tube or tubes, placed with their distal ends in input and/or output vessels of the organ to be perfused, are configured to deliver the perfusion fluid to these vessels. The stent presses the tube or tubes into the wall of the adjacent blood vessel, thereby preventing exchange of fluids from the input and/or output vessels of the organ with blood of the adjacent blood vessel. As a result, the systemic blood, flowing through the inside of the stent, is essentially isolated from the fluid perfusing the organ.

This fourth system could also be used to isolate cells affected with cancer. Because such cells require large amounts of oxygen, they build a network for assuring a relative large blood supply and discharge. The fourth system could be used to block this blood flow, thereby largely isolating the cancer cells and allowing perfusion of them, to a large extend without burdening the not-affected cells of the organ or the rest of the body.

The fifth system, as illustrated in FIG. 4E comprises a tube and a fixation means made of a biocompatible material or materials. The tube is liquid impermeable and is also characterized in that its distal end is formed as a cup or spoon. Furthermore, the tube comprises a flush opening in the concave wall of the cup or spoon form.

Positioning of this system can occur in two steps. First the tube is placed by means of an introducer. Preferably the tube is contained inside the introducer and expands to its cup or spoon form after rejection. The expanded distal end of the tube can then be manoeuvred to its exact position where after the fixation means is released from the introducer and fixates the tube at that position. Said fixation means can be a spring, a tube, a cylinder, a metal or synthetic wire adopting the shape of a spool, or any other means suitable for achieving said goal.

Said fifth system can be used for minimally invasive isolation and perfusion of an organ. Therefore the tube is positioned into the blood vessel and held at its place by the fixation means. The tube is placed in such that its distal end blocks the inflow and/or outflow of blood from main input and/or output vessels into the adjacent vessel. The cup or spoon formed distal end of the tube defines a cavity isolated from the systemic blood flowing through the narrowed path in the adjacent vessel. A lumen extending through the tube defines a flow path for the perfusion fluid, thereby guiding the perfusion fluid through the flush opening in the concave wall of the cup or spoon form into the isolated cavity, allowing isolated perfusion of the organ.

One embodiment of the present invention is a kit comprising a device as defined above, and one or more of the following:
- an occlusion device, with perfusion capacity as an option for the HA,
- an occlusion device, with options for perfusion and shunting,
- one or more perfusion lines,
- said perfusion lines in fluid connection with a means for drawing medicament or perfusion fluid into a perfusion circuit, and
- said perfusion lines in fluid connection with at least one connector for drawing medicament or perfusion fluid into a perfusion circuit, said connector being specific to a particular medicine container.

What is claimed is:

1. A retrievable medical device for the delivery of medical treatment fluid to body vessels, having a distal and a proximal end, comprising a self-expanding, hollow tubular member and a delivery catheter suitable for deploying a self-expanding tubular member, wherein:
    the tubular member comprises a liner made from liquid-impermeable material and a liquid permeable carrier made of braided wire mesh,
    the tubular member is configured to expand radially to form a central part flanked by two annular ridges—a distal annular ridge and a proximal annular ridge, which central part is adapted to form an annular lumen in the vessel, said tubular member has a dumbbell or hourglass shape in the expanded condition in which the central part radially expands to a lesser degree compared to the annular ridges,
    the tubular member comprises a liquid-impermeable area, defined at least by the region flanked by the annular ridges,
    the tubular member comprises two liquid-permeable regions, one distal to the distal annular ridge and one proximal to the proximal annular ridge, so forming a passageway between the distal end and the proximal end of the tubular member for the flow of fluid, the proximal end of the tubular member is attached to the distal end of the delivery catheter, the proximal end is closed but is disposed with a liquid-permeable region devoid of the liner, the distal end of the tubular member is open-mouthed, a wall of the tubular member, in the liquid-impermeable area is disposed with one or more fluid ports for the passage of treatment fluid, and the catheter comprises an inner tube, an outer tube surrounding at least a portion of the length of the inner tube, and a pusher means for deployment of the tubular member, wherein said inner tube is in fluid connection with the one or more fluid ports.

2. Medical device according to claim 1, wherein the liquid-permeable carrier is configured to adopt an essentially cylindrical state when compressed, and to self-expand radially to form a central part flanked by two annular ridges, the liner is attached to the wall of the tubular member, which provides the liquid impermeable area.

3. Medical device according to claim 2, wherein the carrier is made from a surgical wire that is: an alloy comprising Cobalt, Chromium, Nickel, Molybdenum and Iron, or nitinol, or a surgical wire in accordance to the standard ASTM F 1058.

4. Medical device according to claim 2, wherein the carrier is laser cut.

5. Medical device according to claim 2, wherein the carrier is made from any of polycarbonate polyurethane formulation, polytetrafluoroethylene, polyurethane, silicone or polyethylene terephthalate polymer.

6. Medical device according to claim 1, wherein the pusher means being:

a pusher rod disposed between the inner tube and the outer tube, or formed from the wall of the inner tube, the pusher means being adapted for axial movement relative to the outer tube, and the proximal end of the tubular member being attached to the distal end of the pusher means, and disposed within the outer tube in the compressed state.

7. Medical device according to claim 1, wherein the inner tube is configured for the passage of treatment fluid.

8. Medical device according to claim 1, wherein the inner tube is further configured to receive a guidewire.

9. Medical device according to claim 1, wherein the inner tube of the catheter is in fluid connection with the one or more ports, using a bridging tubing.

10. Medical device according to claim 1, wherein the tubular member is configured to create a fluid impermeable annular cavity between said device and the inner wall of the vessel.

11. Medical device according to claim 1, wherein the proximal end of the tubular member is non-releasably attached to the distal end of the delivery catheter.

12. A kit comprising:

a device as defined in claim 1, and one of more of the following:

an occlusion device for the hepatic artery, optionally with perfusion capacity, an occlusion device, with options for perfusion and shunting, one or more perfusion lines, one or more perfusion lines in fluid connection with a means for drawing medicament or perfusion fluid into a perfusion circuit, and one or more perfusion lines in fluid connection with at least one connector for drawing medicament or perfusion fluid into a perfusion circuit, said connector being specific to a particular medicine container.

13. A method for minimal invasive and repeatable organ perfusion of a living being comprising positioning the device of claim 1 into the inferior vena cava, thereby:

a. blocking the flow path of blood in the inferior vena cava;

b. providing a flow path for the blood through the passageway of the device;

c. creating an isolated cavity between the medical device and the wall of the vena cava, which is in contact with the liver by the hepatic veins; and d. delivering the perfusion fluid to or from this cavity by means of the delivery catheter.

14. The method according to claim 13, further comprising the step of withdrawing the device after perfusion.

* * * * *